United States Patent [19]

Sugasawa et al.

[11] 4,186,144
[45] Jan. 29, 1980

[54] PROCESS FOR THE PRODUCTION OF CYANOPINACOLONE

[75] Inventors: Tsutomu Sugasawa, Kobe; Tatsuo Toyoda, Osaka; Kazuyuki Sasakura, Omihachiman; Shiro Ueda, Osaka; Akira Takase, Kobe; Katsuto Okuno, Matsubara; Ichiro Ishizuka; Shinzaburo Sumimoto, both of Osaka, all of Japan

[73] Assignee: Shionogi & Co., Ltd., Osaka, Japan

[21] Appl. No.: 897,001

[22] Filed: Apr. 17, 1978

[30] Foreign Application Priority Data

May 10, 1977 [JP] Japan .................................. 52-53343

[51] Int. Cl.$^2$ ............................................. C07C 121/34
[52] U.S. Cl. ................................ 260/465.1; 260/465.6
[58] Field of Search ...................................... 260/465.1

[56] References Cited

U.S. PATENT DOCUMENTS 4,062,861  12/1977  Yukinaga et al. .................. 71/88 X

OTHER PUBLICATIONS

C. A., Wahlberg, 15 (1921), 1490$^8$.
C. A., Mousseron, et al., 45 (1951), 1967$^d$.
C. A., Iimura, 53 (1959), 5185$^d$.
Schaefer, et al., J. Org. Chem., 28 (1963), p. 1128.
C. A., Jastoni et al., 43 (1949), 2936$^f$.

*Primary Examiner*—Joseph P. Brust
*Attorney, Agent, or Firm*—Birch, Stewart, Kolasch and Birch

[57] ABSTRACT

Cyanopinacolone is produced by reacting pinacolone with about 1.0 to about 1.2 molar equivalents of chlorine in methanol and further reacting the resulting monochloropinacolone with about 1.0 to about 1.2 molar equivalents of an alkali metal cyanide in methanol.

7 Claims, No Drawings

PROCESS FOR THE PRODUCTION OF CYANOPINACOLONE

The present invention relates to a novel process for the production of cyanopinacolone, a synthetic intermediate for 1,1-dimethyl-3-(5-t-butyl-3-isoxazolyl)urea (U.S. Pat. No. 4,062,861) and the like herbicides. The references 1) and 2) disclose processes for the production of monochloropinacolone and the references 1) and 3) disclose processes for the production of cyanopinacolone as follows:

(1) Imura, Nippon Kagaku Zasshi (Journal of the Chemical Society of Japan), 78, 48 (1957);

(2) Schaefer et al., J. Org. Chem., 28, 1128 (1963); and (3) Jastoni et al., Chemical Abstracts, 43, 2936 f (1949).

However, the synthetic processes disclosed in these references run in a low yield of below 50%, and the processes disclosed in references (1) and (3) require an excess amount of alkali metal cyanide. Thus, these processes are less satisfactory on the industrial scale. After diligent investigation for much improved synthetic processes, the present inventors have discovered that by using methanol as a solvent in the above reaction system, the reaction proceeds selectively to give a much higher yield. As a result the present invention has been successfully reduced to practice.

The present invention relates to a process for the production of cyanopinacolone (IV) which comprises reacting pinacolone (I) with about 1.0 to about 1.2 molar equivalents of chlorine in methanol and further reacting the resulting monochloropinacolone (II) with about 1.0 to about 1.2 molar equivalents of an alkali metal cyanide in methanol.

The objective product (IV) of this invention can be obtained as shown in the following reaction scheme:

First step t-Bu-CO—CH$_3$ $\xrightarrow{\text{Cl}_2}{\text{MeOH}}$ (I)

t-Bu-CO—CH$_2$Cl + t-Bu-CO—CHCl$_2$ (II)  (III)

Second step t-Bu-CO—CH$_2$Cl $\xrightarrow{\text{NaCN}}{\text{MeOH}}$ (II)

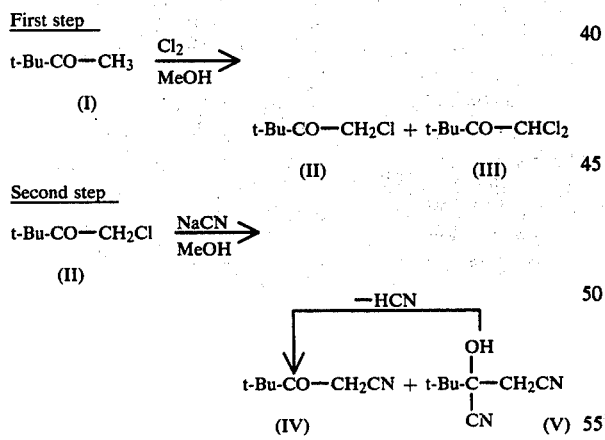

(wherein Me and t-Bu represent methyl and tertiary butyl groups, respectively).

The reaction of the first step can be carried out by introducing about 1.0 to about 1.2 molar equivalents of chlorine into a solution of pinacolone (I) in methanol. The chlorination proceeds within a short period (about 2 to 3 hours) by using liquid or gaseous chlorine at room temperature or with ice cooling and produces the objective monochloropinacolone (II) in an almost selective yield (e.g. about 90%), while the production of a by-product, dichloropinacolone (III), is controlled down to a very small extent (below 0.5%). The product (II) can be subjected to the second step without any isolation or purification of the first step product.

The second step can be carried out by reacting the above obtained monochloropinacolone (II) with about 1.0 to about 1.2 molar equivalents of an alkali metal cyanide in methanol. The reaction is carried out with heating at around the boiling point of methanol for a few hours. By evaporating hydrocyanic acid and methanol from the reaction mixture under atmospheric pressure, the reaction equilibrium shifts to convert a by-product, 2-hydroxy-2-butylsuccinonitrile (V), into cyanopinacolone (IV). Furthermore, almost all the remaining 2-hydroxy-2-t-butylsuccinonitrile (V) can be converted into said cyanopinacolone (IV) by adding a catalytic amount of an alkali metal salt of a weak acid (e.g. sodium hydrogen carbonate) or of hydrofluoric acid (e.g. sodium fluoride) to a solution of the reaction products in an extract solvent (e.g. benzene, toluene, methylene chloride) and concentrating the resulting mixture under atmospheric pressure. Such an alkali cyanide includes sodium cyanide, potassium cyanide and the like.

Industrial advantages of the present invention are shown as follows:

(1) the yield of the main products, monochloropinacolone (II) and cyanopinacolone (IV), can be raised due to the suppressed formation of the by-products, dichloropinacolone (III) and 2-hydroxy-2-t-butylsuccinonitrile (V), respectively;

(2) the operation is simple, and the above two steps can be carried out continuously. In such a case a higher overall yield (e.g. about 85%) can also be attained;

(3) the raw materials, namely pinacolone, chlorine and methanol, are each easily available at low prices;

(4) the commercially available aqueous solution of sodium cyanide, potassium cyanide or the like can be safely used; and (5) without taking any anti-pollution procedures with chlorine and hypochloric acid, the hydrocyanic acid contained in the evaporated methanol can be recycled by basifying the waste fluid with an aqueous caustic alkali solution and concentrating to regenerate said aqueous alkali metal cyanide for a new run. The thus obtained cyanopinacolone (IV) can be easily converted, for example, into 1,1-dimethyl-3-(5-t-butyl-3-isoxazolyl)urea (VI), a potent herbicide, according to the following reaction scheme:

t-Bu-CO—CH$_2$CNN $\xrightarrow{\text{EtOH}}{\text{HCl}}$ (IV)

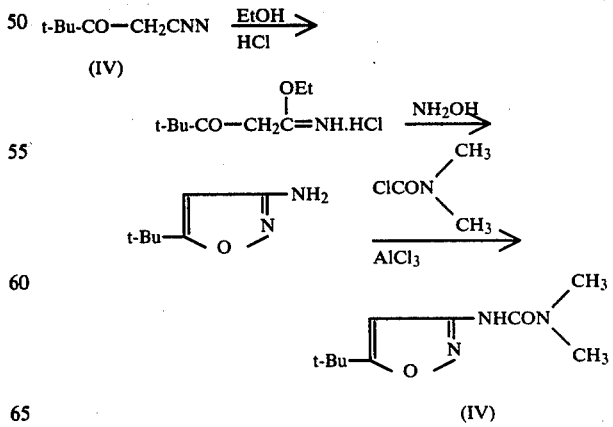

(wherein Et represents an ethyl group and t-Bu has the meaning given above.)

Presently-preferred and practical embodiments of the present invention are illustratively shown in the following examples.

EXAMPLE 1

(1) Into a solution of pinacolone (20 g, 0.20 mol) in methanol (60 ml) is introduced chlorine (14.18 g, 0.20 mol) with ice cooling and stirring over a period of 2.5 hours. After evaporating the solvent under atmospheric pressure, the residue is mixed with ice water and shaken with ether. The ethereal layer is washed with 2 N aqueous sodium carbonate and brine in that order, dried over magnesium sulfate and then the ether is evaporated. The residue is distilled under a reduced pressure to give monochloropinacolone (24.36 g) boiling at 78°–79° C./23 mmHg. Yield is 92%. The product contains 0.3% of dichloropinacolone as a contaminant.

(2) To a solution of the above obtained monochloropinacolone (10 g, 74.3 m mol) in methanol (50 ml is added an aqueous solution (10.5 ml) containing sodium cyanide (4.50 g, 74.3×1.2 m mol). After refluxing the mixture for 1 hour, a part of the methanol (33 ml) is evaporated over a period of 1 hour. The residue is dissolved in 6 N aqueous sodium hydroxide (5 ml) and ice pieces and washed with ether to remove an oily neutral material (837 mg). The alkaline aqueous layer is poured into 3 N hydrochloric acid under ice cooling and shaken with methylene chloride. The organic layer is washed with water, dried and concentrated to give cyanopinacolone (8.4 g) as crystals. Yield is 90%. The product contains 3.58% of 2-hydroxy-2-t-butylsuccinonitrile as a contaminant.

EXAMPLE 2

To a solution of pinacolone (100.16 g, 1 mol) in methanol (300 ml) is introduced gaseous chlorine (70.91 g, 1 mol) at 15–20° C. over a period of 1 hour. The reaction mixture is neutralized with a 48% solution of sodium hydroxide in methanol (285 ml) and then aqueous solution of sodium hydrogen carbonate (4.20 g) in that order. After dilution with methanol (40 ml), the resulting mixture is mixed with an aqueous solution (137 ml) of sodium cyanide (58.81 g, 1.2 mol) and refluxed for 1 hour. The methanol is evaporated under atmospheric pressure over a period of 1.5 hours. The residue is mixed with a 4% aqueous sodium hydroxide (650 g) solution and shaken with benzene (300 ml) to remove neutral material (10.78 g). Hydrochloric acid (35%) (92.60 g) is poured into said alkaline aqueous layer below 15° C., and the mixture is shaken with benzene (750 ml). The benzene layer is washed with water, then mixed with an aqueous solution (44 ml) of sodium hydrogen carbonate (0.66 g), and the benzene layer is evaporated under atmospheric pressure. A solution of the residue is adjusted to pH 7.0 by stirring with benzene (142 ml), water (30 ml) then 35% hydrochloric acid (0.37 g). The benzene layer is dried and concentrated to give cyanopinacolone (106.70 g) as crystals melting at 64° to 67° C. Yield is 85%. The product contains only 0.09% of 2-hydroxy-2-t-butylsuccinonitrile as a contaminant.

What is claimed is:

1. A process for the production of cyanopinacolone which consists essentially of reacting pinacolone with about 1.0 to about 1.2 molar equivalents of chlorine in methanol and further reacting the resulting monochloropinacolone with about 1.0 to about 1.2 molar equivalents of an alkali metal cyanide in methanol.

2. The process according to claim 1, wherein the chlorination is carried out at room temperature or under cooling.

3. The process according to claim 1, wherein the alkali metal cyanide is sodium cyanide.

4. The process according to claim 1, wherein the reaction of said alkali metal cyanide is carried out with heating at around the boiling point of methanol.

5. The process according to claim 4, wherein a by-product formed during the reaction, 2-hydroxy-2-t-butylsuccinonitrile, is converted into cyanopinacolone by adding a catalytic amount of sodium hydrogen carbonate or sodium fluoride to an extract solution of the reaction products in benzene and concentrating the resulting mixture under atmospheric pressure.

6. A process for the production of cyanopinacolone which consists essentially of reacting pinacolone with about 1.0 to about 1.2 molar equivalents of chlorine in methanol at around room temperature or with ice cooling for a period of up to about 3 hours and further reacting the resulting monochloropinacolone with about 1.0 to about 1.2 molar equivalents of an alkali metal cyanide in methanol at a temperature around the boiling point of methanol for a time sufficient to produce said cyanopinacolone.

7. The process according to claim 6, wherein a by-product formed during the reaction, 2-hydroxy-2-t-butylsuccinonitrile, is converted into cyanopinacolone by adding a catalytic amount of sodium hydrogen carbonate or sodium fluoride to an extract solution of the reaction products in benzene and concentrating the resulting mixture under atmospheric pressure.

* * * * *